(12) United States Patent
Clemente

(10) Patent No.: US 10,820,637 B2
(45) Date of Patent: Nov. 3, 2020

(54) SELF-CONTAINED AIR DISTRIBUTION SYSTEM

(71) Applicant: Roger Clemente, Hazlet, NJ (US)

(72) Inventor: Roger Clemente, Hazlet, NJ (US)

(*) Notice: Subject to any disclaimer, the term of this patent is extended or adjusted under 35 U.S.C. 154(b) by 289 days.

(21) Appl. No.: 15/860,263

(22) Filed: Jan. 2, 2018

(65) Prior Publication Data
US 2019/0200689 A1   Jul. 4, 2019

(51) Int. Cl.
| | | |
|---|---|---|
| *A41D 13/002* | (2006.01) | |
| *A61F 7/02* | (2006.01) | |
| *A41D 13/005* | (2006.01) | |
| *A61F 7/00* | (2006.01) | |

(52) U.S. Cl.
CPC ...... *A41D 13/0025* (2013.01); *A41D 13/0053* (2013.01); *A61F 2007/008* (2013.01); *A61F 2007/0018* (2013.01); *A61F 2007/0063* (2013.01); *A61F 2007/0068* (2013.01); *A61F 2007/0228* (2013.01); *A61F 2007/0233* (2013.01); *A61F 2007/0234* (2013.01)

(58) Field of Classification Search
CPC ............ A41D 13/0025; A41D 13/0053; A41D 27/28; A41D 13/002; A41D 13/0158; A61F 2007/0018; A61F 2007/0063; A61F 2007/0068; A61F 2007/008; A61F 2007/0228; A61F 2007/0233; A61F 2007/0234; F24F 2221/38; F24F 7/06
USPC ........................ 454/251, 170, 283, 286, 344
See application file for complete search history.

(56) References Cited

U.S. PATENT DOCUMENTS

| | | | |
|---|---|---|---|
| 6,823,678 B1 * | 11/2004 | Li ...................... | A41D 13/0025 62/259.3 |
| 2016/0128396 A1 * | 5/2016 | Clemente ........... | A41D 13/0056 62/259.3 |

* cited by examiner

*Primary Examiner* — Grant Moubry
*Assistant Examiner* — Ryan L Faulkner
(74) *Attorney, Agent, or Firm* — Patterson + Sheridan, LLP

(57) ABSTRACT

A self-contained portable air distribution system for cooling an individual by the movement of intake and exhaust air flow streams over an individual. The system includes a portable rechargeable battery operated fan that produces both an inlet intake and outlet exhaust air flow streams that provides a cooling effect by evaporating body moisture as it passes over the body.

20 Claims, 5 Drawing Sheets

SELF-CONTAINED AIR DISTRIBUTION SYSTEM

BACKGROUND OF THE INVENTION

1. Field of the Invention

The present invention relates to a thermal management air distribution system that uses a fan's intake and exhaust air flow stream to cool the body of an individual to prevent heat stress and fatigue by evaporating body moisture and perspiration when exposed to high ambient temperature. The present air distribution system is described and has a particular cooling and evaporative effect to humans.

2. Description of the Prior Art

Individuals are oftentimes required to perform physical activity or duty in ambient atmosphere which is conducive to perspiration. Construction workers in hot climates oftentimes find themselves in such situations, however, they are not always required to wear heavy equipment, and the situation is such that they can take frequent rest breaks, seek out shaded areas, and hydrate when needed.

Other individuals performing in such ambient temperatures are not often allowed the luxury of rest breaks and the like. These include military personnel, which are often required to wear protective outerwear, such as tactical protective vests and multiple layers of clothing, in addition to the personal military equipment they must carry with them. Similar workers that are involved in hazardous waste clean-up, or firefighting, have to wear protective outerwear, such as protective gloves, boots, and outer clothing, together with protective headgear and face masks. These individuals are subjected to substantial fluid loss due to the clothing they are wearing, the equipment they are carrying, and the ambient thermal atmosphere.

Therefore there has been a need for a self-contained apparatus which can be worn by an individual in such conditions which is light weight, comfortable, and distributes air flow about the body of the individual that may include the chest, back and head. Such a system needs to be responsive of the body and not be subject to shut down or collapse by the movement of the body. That is, the individual should be able to lie on his stomach, lie on his back, or sit with his back against a rigid object without the system shutting down or ceasing the distribution and flow of air about the body.

Cooling garments have been widely explored and include systems which attempt to blot the moisture and perspiration from the body, as well as incorporation an air flow system which is incorporated within a protective vest to distribute air yet such a system compromises the performance of the protective vest.

There are numerous personal cooling systems to prevent heat overload and stress. The advantages, methods and construction have been well documented. Currently, vest or garment systems that keep the body cool use phase change material, air, compressed gas, ice, water or a circulating refrigerated liquid. U.S. Pat. No. 6,257,011 B1 to Siman-Tov, et al. teaches an air moving channel sheet capable of absorbing evaporative liquid. U.S. Pat. No. 6,874,332 B2 to Forgach teaches a vest having a fan to discharge air through its elongated housing. U.S. Pat. No. 5,533,354 to Pirkle teaches a harness constructed of perforated tubing which uses a gas to circulate air over the body. U.S. Pat. No. 9,308,121B2 to Clemente teaches a helical air distribution system.

SUMMARY OF THE INVENTION

A self-contained portable air distribution system for cooling an individual by the movement of intake and exhaust air flow streams over an individual. The system includes a portable rechargeable battery operated fan that produces both an inlet intake and outlet exhaust air flow streams that provides a cooling effect by evaporating body moisture as it passes over the body.

An advantage of the present invention is an air distribution system having a portable self-contained battery operated fan that produces an intake and exhaust air flow stream that cools the body by evaporating body moisture.

A further advantage of the present invention is a novel light weight flexible air distribution system that produces an air flow stream which can be worn directly against the torso or over or under the clothing, garments, protective outerwear or equipment of an individual without clogging or shut down.

A still further advantage of the present invention is a novel flexible air distribution system which allows the individual to perform normal bodily movement, such as sitting, lying prone, lying supine, without affecting the integrity of the system or interrupting the flow of air.

A still further advantage of the present invention is a novel air distribution system which uses both the intake and exhaust air flow stream to cool the body by evaporating body moisture.

A still further advantage of the present invention is a novel air distribution system which can be independently worn about the body, with or without garments, allowing the intake and exhaust discharge air stream to be distributed about the desired portion of the body.

A still further advantage of the present invention is a novel flexible air distribution system which is responsive to the movement of the body of the individual.

A still further advantage of the present invention is a novel air distribution system that does not need garments or vests to hold it in place.

A still further advantage of the present invention is a novel air distribution system that evaporates skin moisture without garments or vest wrap around an individual.

A still further advantage of the present invention is an air distribution system that evaporates body moisture directly or indirectly by the movement of air through a fans intake and exhaust outlet.

Further, still another advantage of the present invention is an air distribution system having a light weight micro fan assembly having a small footprint.

Still further advantage of the present invention is a novel air distribution system that is optionally held in place by a lanyard, a clip, fastener, garment, harness, a strap, magnets or hook and loop fasteners.

A further advantage of the present invention is a novel air distribution system using an air flow stream that optionally travels over a water evaporating cold membrane or other temperature control device to provide climate controlled air.

Still a further advantage of the present invention is a novel portable air distribution system using a holder with a rechargeable battery.

A further advantage of the present invention is a novel air distribution system that can cool the upper or lower torso of the body of an individual.

Still a further advantage of the present invention is a novel air distribution system having resilient open intake and exhaust air passageways that does not shut down or cut off air supply when worn against the skin, over or under garments, clothing or under protective suits.

A further advantage of the present invention is a novel air distribution system optionally having a ducted dual axial counter rotating fan assembly that produces an intake and exhaust air flow stream.

Still a further advantage of the present invention is a novel air distribution system that is fully functional when worn over, under or within a garment.

Another advantage of the present invention is a more efficient air distribution system that uses both intake and exhaust air flow streams for cooling as compared to conventional systems which only use one method not both.

A further advantage of the present invention is an air distribution system that utilizes both the intake and exhaust air flow streams, generated by a fan, to cool a person's body as the air flow streams travel horizontally or vertically in a tapered, conical, fluted hourglass path.

BRIEF DESCRIPTION OF THE DRAWINGS

These and other objects of the present invention will become apparent, particularly when taken in light of the following illustrations wherein.

DETAILED DESCRIPTION OF THE INVENTION

None of the conventional systems described above have the capability of using a portable motorized fan that uses both the intake suction and discharge outlet air flow streams to cool the body of an individual by evaporating body moisture. The presently disclosed lightweight miniature personal system allows the intake and discharge flow of air to circulate about the body of an individual, cooling the body by providing an air flow stream created by both the movement of inlet suction air and the pressurized exhaust outlet air. As both of the air flow streams move over the body it creates a cooling effect that evaporates body moisture and perspiration.

In one example, the personal system comprises a battery operated ducted counter rotating duel axial fan assemblies, arranged in series, having an inlet and outlet that moves air in one direction through both fan assemblies. In operation, the fan assemblies, draws air in through a fan intake and exits the pressurized fan outlet.

Figure 1:
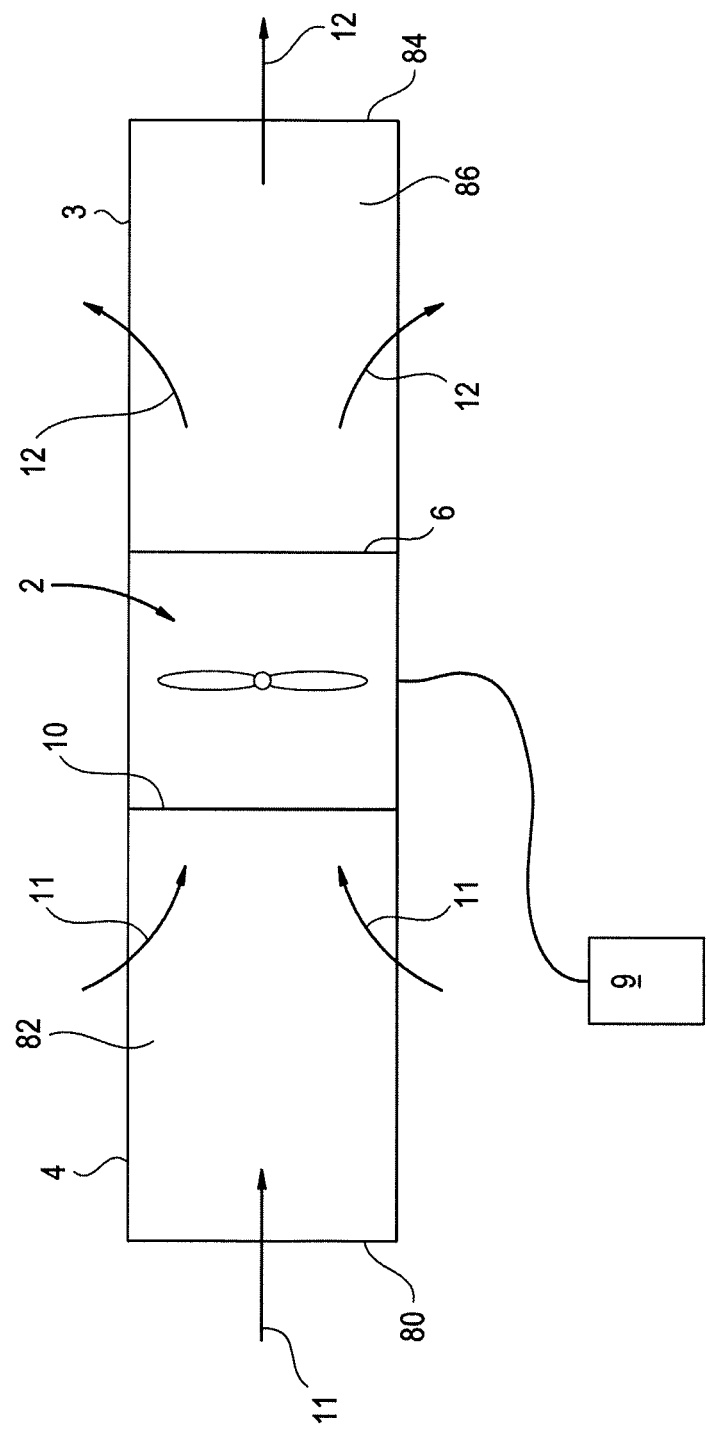
FIG. 1 is a schematic depiction of a self-contained air distribution system of the present invention.
Figure 2:
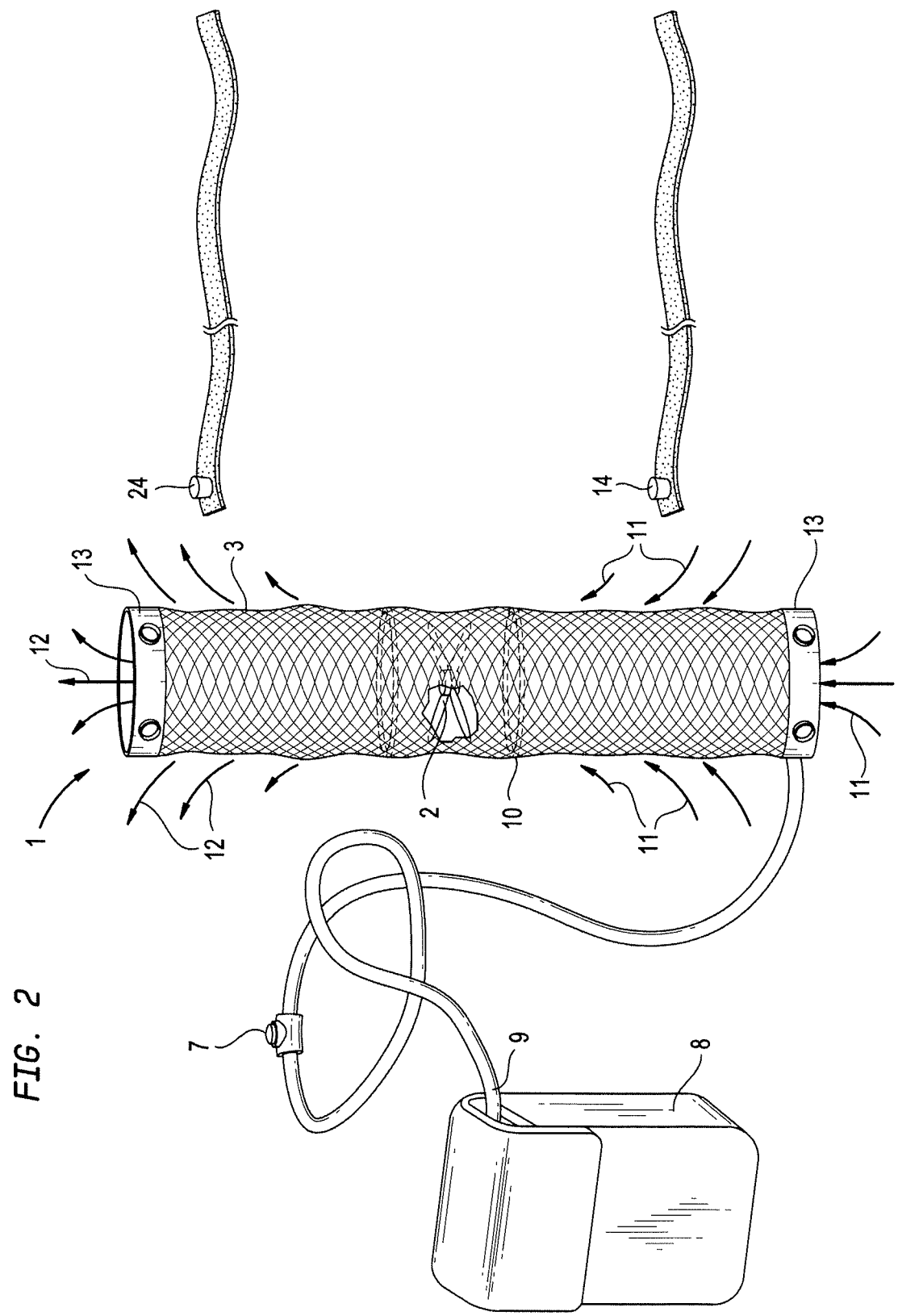
FIG. 2 is a front view of the self-contained air distribution system of the present invention.

FIG. 1 is a schematic depiction of a self-contained air distribution system 1 of the present invention. FIG. 2 is a front view of the self-contained air distribution system 1 of the present invention which can be located on different parts of a user's body. Although the user is described herein as a person, the self-contained air distribution system 1 may be adapted for other uses, such as with dogs, horses, and cows, among other animals.

The self-contained air distribution system 1 is described initially with respect to its adaption to use by a human individual who is required to perform physical activity in ambient atmosphere which is conducive to excessive perspiration. This would include construction workers, astronauts, military personnel, hazardous waste clean-up individuals, fire fighters, and others who oftentimes are required to wear substantial protective clothing and equipment. The distribution of air by the system will have a cooling and evaporative effect on the individual wearing the system.

The self-contained air distribution system 1 as illustrated in FIGS. 1 and 2 is adapted for human use. The air distribution system 1 is comprised of a portable battery operate fan assembly 2 powered by a rechargeable battery 9. The battery 9 resides in a holder 8 that may be located remotely from the self-contained air distribution system 1. The rechargeable battery 9 is coupled to the fan assembly 2 by electrical leads. Fan assembly 2 having an inlet 10 and outlet 6 are connected to air passageway conduits 4 and 3 that are integral to the system 1.

The air inlet conduit 4 includes an inlet opening 80 located opposite the inlet 10 of the fan assembly 2, and a conduit sidewall 82. The conduit sidewall 82 is generally fabricated from a flexible material and is configured to allow air to be drawn through the conduit sidewall 82 by operation of the fan assembly 2. The conduit sidewall 82 has a property that allows air to pass radially through the conduit sidewall 82. For example, the conduit sidewall 82 may be porous, perforated, slotted, have apertures, spiral wound with gaps, or other suitable arrangement or material that allows air to pass radially through the conduit sidewall 82. The material of the conduit sidewall 82 may also be resilient. Thus, the conduit sidewall 82 is made from a polymeric materials or other suitable material not subject to shut down, clogging or collapse when the system 1 is in use. The suction air being drawn radially through the conduit sidewall 82 provides cooling along the entire length of the sidewall 82, as opposed to solely drawing air into the fan assembly 2 from the inlet opening 80 of the sidewall 82 disposed at the end of the sidewall 82 farthest from the fan assembly 2.

Similarly, the air conduit 3 includes an outlet opening 84 located opposite the outlet 6 of the fan assembly 2, and a conduit sidewall 86. The conduit sidewall 86 is generally fabricated from a flexible material and is configured to allow air to be drawn through the conduit sidewall 86 by operation of the fan assembly 2. The conduit sidewall 86 has a property that allows air to pass radially through the conduit sidewall 86. For example, the conduit sidewall 86 may be porous, perforated, slotted, have apertures, spiral wound with gaps, or other suitable arrangement or material that allows air to pass radially through the conduit sidewall 86. The material of the conduit sidewall 86 may also be resilient. Thus, the conduit sidewall 86 is made from a polymeric materials or other suitable material not subject to shut down, clogging or collapse when the system 1 is in use. The pressurized air being forced radially through the conduit sidewall 86 provides cooling along the entire length of the sidewall 86, as opposed to solely flowing air out of the fan assembly 2 through a single outlet opening 84 disposed at the end of the sidewall 86 farthest from the fan assembly 2.

In one example, a distance between the inlet opening 80 and the outlet opening 84 is generally less than the height of a user's torso 30. For example, the distance between the inlet opening 80 and the outlet opening 84 may be less than 16 inches. When in use, the air travels into the inlet 10 of the fan assembly 2 through both the inlet opening 80 and the conduit sidewall 82, and exits the outlet 6 of the fan assembly 2 through both the outlet opening 84 and the conduit sidewall 86. Thus, both the inlet 10 and outlet 6 of fan assembly 2 alone or combine with open air passageway conduits 4 and 3 can produce air flow streams (shown by arrows 11 and 12) about torso 30 of a user creating a cooling effect by evaporating body moisture.

The air distribution system 1 may be disposed under or within a garment 20. As used herein, the phrase "under the garment" means that an item is disposed between the garment 20 and the torso 30 of a user, as opposed to be located vertically below the garment 20. In on example, the air distribution system 1 is held in place by using magnet's 14 and 24 which can be place over or under garment 20 and attached to metal clips 13. In some cases, a magnet 24 may be attached to a strap or lanyard 18 around the neck of the user for holding air distribution system 1 by metal clip 13. Alternatively, the air distribution system 1 may be held in place by using hook and loop fasteners, a clip, fastener, garment, harness, or by other suitable technique.

In operation, when fan assembly 2 is energized by battery 9, it creates an intake air flow stream 11, which is then drawn into open air conduit 4 into inlet 10 of fan assembly 2. It then exhaust through fan outlet 6 and moves through open air conduit 3 creating an exhaust air flow stream 12. As air flow streams 11 and 12 move, circulate and pass over a person torso 30, shown in FIG. 3, it creates a cooling affect by evaporating body moisture.

Figure 3:
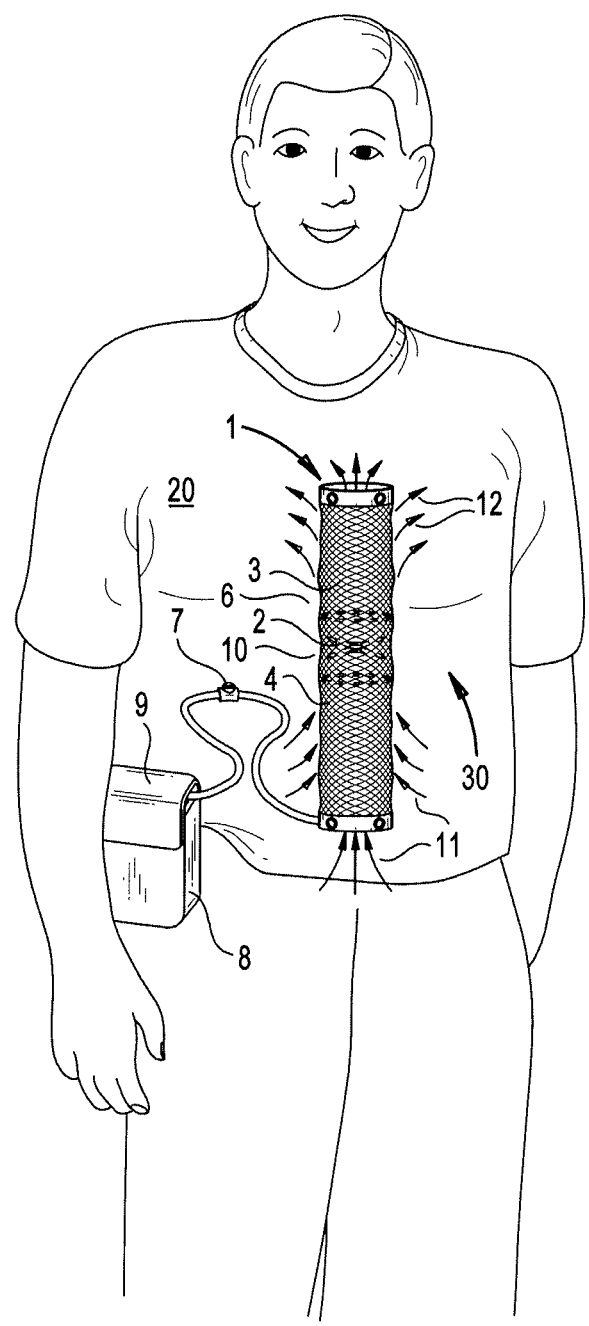
FIG. 3 is a front view of the self-contained air distribution system positioned about the torso of an individual.

FIG. 3 is a front view of the self-contained air distribution system 1 position about the torso 30 of an individual. Air distribution system 1 is changeable in position (i.e., repositionable) and can functionally operate when worn fully, partially, directly or indirectly against an individual's torso 30 or other parts of the body.

For ease of disclosing, FIG. 3 shows the air distribution system 1 worn indirectly about the torso 30 over a garment 20. However, it should be understood that its primary use is to be place directly against the torso 30 under garment 20 or similar shirt, vest, uniform, suit or protective equipment, etc. For example, the self-contained air distribution system 1 of FIG. 3 may be worn below protective outerwear 80, such as a body armor, bullet-proof vest, and hazmat suits, among others.

Continuing to refer to FIG. 3, air distribution system 1 in FIG. 3 is held in place by magnets 24 and 14 [not shown] under garment 20 which are attracted to metal clips 13. The air distribution system 1 may alternatively be secured to the garment 20 by the magnets 24 and 14, pocket or strap coupled to the inside of [not shown] the garment 20, or by another suitable manner.

The air distribution system 1, when placed directly or indirectly against torso 30, is fully functional when energized by on-off switch 7 which connects battery 9 to the motor of the fan assembly 2. In operation, an intake air flow stream 11 is created entering the fan assembly 2 through open air conduit 4 and drawn into fan inlet 10. The air then exits the fan assembly through fan exhaust outlet 6 that discharges an air flow stream 12 through open air conduit 3. As air flow streams 11 and move about the torso 30 or other parts of the body, it creates a cooling affect by evaporating body moisture.

Figure 4:
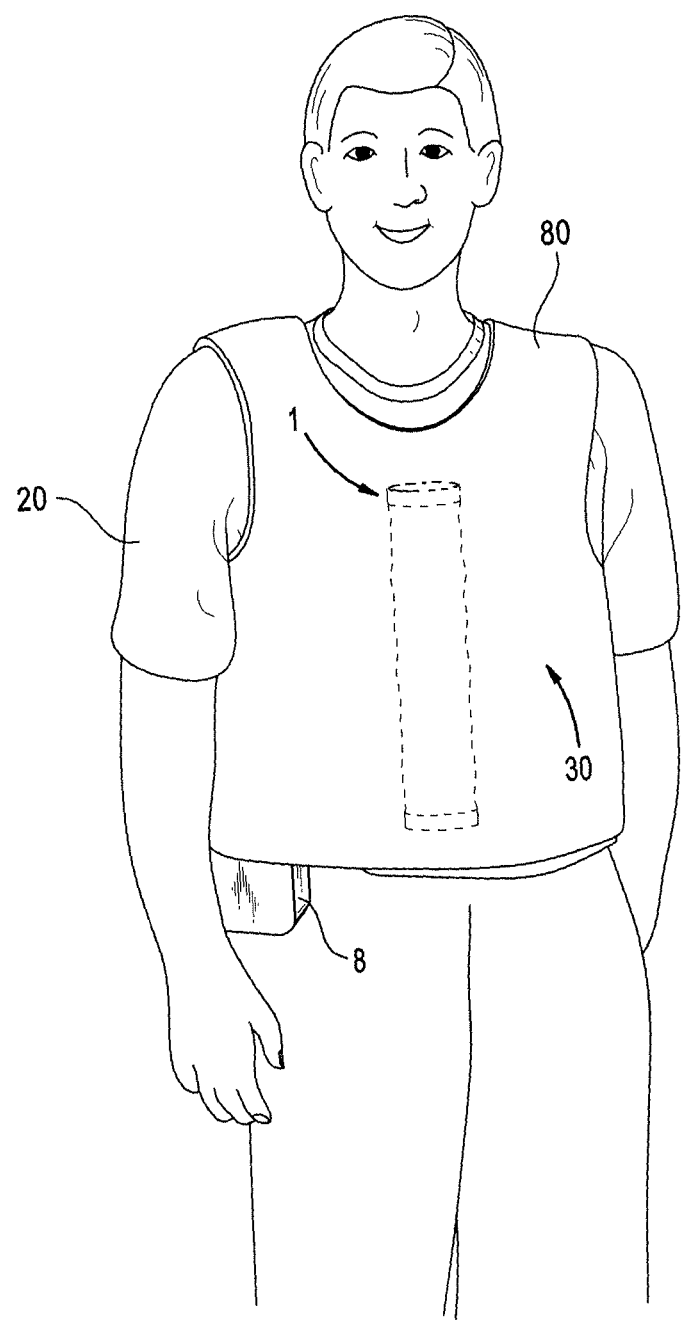
FIG. 4 is a front view of the self-contained air distribution system of FIG. 3 illustrated below protective outerwear.
Figure 5:
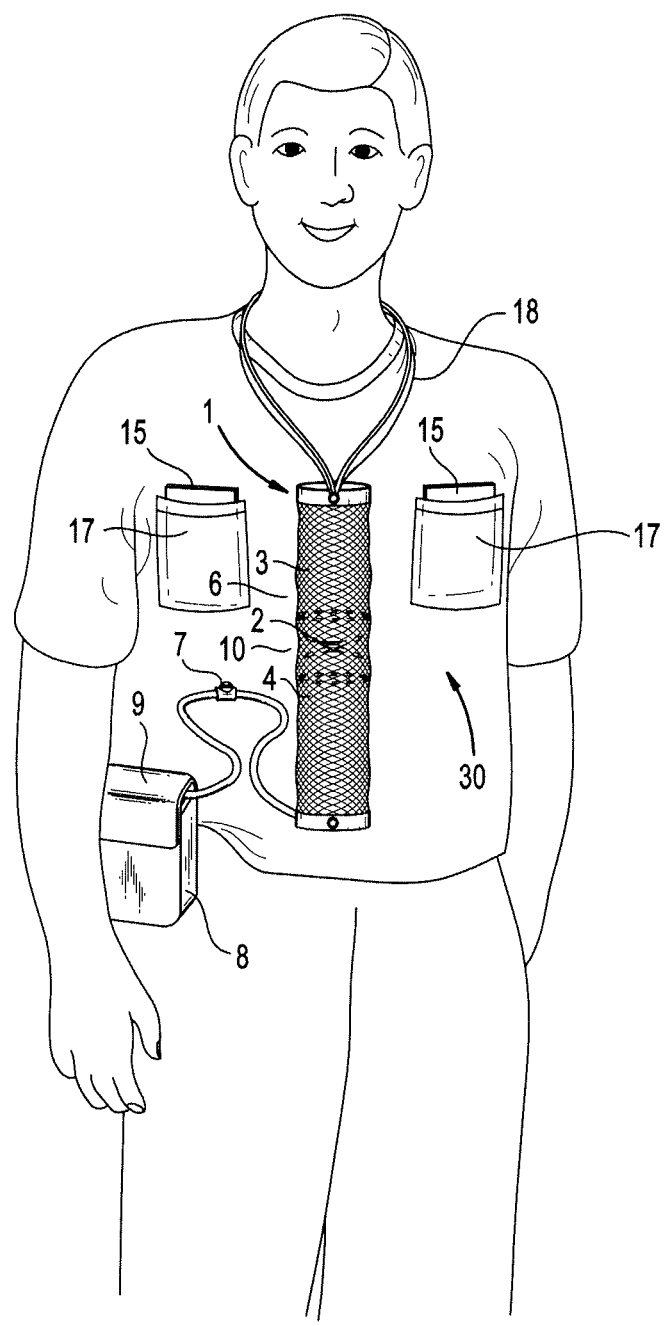
FIG. 5 is a front view of the self-contained air distribution system having a water evaporation or cold membrane.

FIG. 5 is a front view of the changeable self-contained air distribution system 1 placed about the torso 30. The changeable self-contained air distribution system 1 may be worn over a garment 20, and/or worn under protective outerwear such as shown in FIG. 4. In this embodiment, garment 20 is comprised of pockets 17 that contain a temperature control device 15. When the fan assembly 2 is energize, air flow stream 12 exits open air conduit 3 and passes over pockets 17. As the air flow stream 12 passes over pocket 17 containing one or more temperature control devices 15. The temperature control device 15 may be a evaporative cooler, water bubbler, a cold membrane (such as an ice pack) and the like, which functions to reduce the temperature of the air flow stream to a temperature lower than ambient, which provides an additional cooling affect as it passes over an individual. The self-contained air distribution system 1 and temperature control device 15 are repositionable and can be placed over in different positions or under garment 20.

Therefore, while the present invention has been disclosed with respect to the preferred embodiments thereof, it will be recognized by those of ordinary skill in the art that various changes and modifications can be made without departing from the spirit and scope of the invention. It is therefore manifestly intended that the invention be limited only by the claims and the equivalence thereof.

What is claimed is:

1. A self-contained air distribution system comprising:
   a battery operated electric fan assembly having an air inlet and an air outlet;
   an inlet conduit having an inlet conduit sidewall coupled to the air inlet of the battery operated electric fan assembly and extending to an inlet opening, the inlet conduit sidewall being open to permit air to flow through the inlet conduit sidewall into the inlet conduit and to the inlet of the battery operated electric fan assembly; and
   an outlet conduit having an outlet conduit sidewall coupled to the air outlet of the battery operated electric fan assembly and extending to an outlet opening, wherein both the inlet conduit and the outlet conduit are configured to move an air flow stream across a body surface.

2. The self-contained air distribution system of claim 1, wherein a distance between the inlet opening and the outlet opening is less than about 16 inches.

3. The self-contained air distribution system of claim 1, wherein the inlet sidewall and inlet opening are configured to allow air to flow therethrough.

4. The self-contained air distribution system of claim 1, wherein the inlet sidewall is comprised of a plurality of air flow apertures formed therethrough.

5. The self-contained air distribution system of claim 4, wherein the inlet sidewall is a mesh, a spiral wound tube or perforated.

6. The self-contained air distribution system of claim 1, wherein the outlet conduit sidewall is configured to permit air to pass therethrough.

7. The self-contained air distribution system of claim 1, wherein the outlet conduit sidewall and the outlet opening are configured to allow air to flow therethrough.

8. The self-contained air distribution system of claim 1, wherein the outlet conduit sidewall is comprised of a plurality of air flow apertures formed therethrough.

9. The self-contained air distribution system of claim 8, wherein the outlet conduit sidewall is a mesh, a spiral wound tube or perforated.

10. The self-contained air distribution system of claim 1 further comprising:
    a temperature control device associated with the self-contained air distribution system, the temperature control device configured to interface with an airstream exiting the electric fan assembly.

11. The self-contained air distribution system of claim 10 wherein the temperature control device comprises:

a water evaporating cold membrane or other temperature control device to provide climate controlled air to cool a body on which the garment is worn.

12. The self-contained air distribution system of claim 11, wherein the outlet conduit sidewall is a mesh, a spiral wound tube or perforated.

13. The self-contained air distribution system of claim 1 further comprising:
a garment having the inlet conduit and the outlet conduit disposed thereunder.

14. The self-contained air distribution system of claim 1 further comprising:
a garment, wherein the inlet conduit and the outlet conduit are disposed above, below, or within the garment.

15. The self-contained air distribution system of claim 14, wherein the air movement is horizontal and vertical.

16. The self-contained air distribution system of claim 1 further comprising:
a lanyard, a clip, fastener, garment, harness, a strap, magnet or hook and loop fastener coupled to at least one of the electric fan assembly, the inlet conduit and the outlet conduit.

17. The self-contained air distribution system of claim 1 further comprising:
a garment having the electric fan assembly disposed thereabout;
wherein the inlet conduit sidewall is configured to draw air into the fan air inlet; and
wherein the outlet conduit sidewall is coupled to the air outlet of the fan assembly, and wherein the outlet conduit is configured to flow air from the fan air outlet when disposed above, within, or under the garment.

18. The self-contained air distribution system of claim 17 further comprising:
a temperature control device coupled to the garment and positioned to interface with air exiting the outlet conduit sidewall.

19. The self-contained air distribution system of claim 1, wherein both the inlet and outlet conduits are configured to be worn directly against the torso or over or under clothing, garments, protective outerwear or protective equipment of an individual without clogging or shutdown.

20. The self-contained air distribution system of claim 19, wherein the self-contained air distribution system is configured to cool a body on which the garment is worn directly or indirectly by movement of air through both the inlet and outlet conduits evaporating body moisture.

* * * * *